United States Patent
Wiand

(10) Patent No.: US 9,987,727 B2
(45) Date of Patent: Jun. 5, 2018

(54) INDUCTION HEATED VACUUM FURNACE FOR MAKING BRAZED DIAMOND DENTAL BURRS

(71) Applicant: Inland Diamond Products Company, Madison Heights, MI (US)

(72) Inventor: Ronald C. Wiand, Troy, MI (US)

(73) Assignee: Inland Diamond Products Company, Madison Heights, MI (US)

( * ) Notice: Subject to any disclaimer, the term of this patent is extended or adjusted under 35 U.S.C. 154(b) by 200 days.

(21) Appl. No.: 14/689,726

(22) Filed: Apr. 17, 2015

(65) Prior Publication Data

US 2015/0298291 A1    Oct. 22, 2015

Related U.S. Application Data

(60) Provisional application No. 61/980,929, filed on Apr. 17, 2014.

(51) Int. Cl.
| | |
|---|---|
| *B24D 3/06* | (2006.01) |
| *B24D 18/00* | (2006.01) |
| *A61C 3/02* | (2006.01) |

(52) U.S. Cl.
CPC ............... *B24D 3/06* (2013.01); *A61C 3/02* (2013.01); *B24D 18/00* (2013.01)

(58) Field of Classification Search
CPC .............. B24D 3/06; B24D 18/00; A61C 3/02
See application file for complete search history.

(56) References Cited

U.S. PATENT DOCUMENTS

| | | | | |
|---|---|---|---|---|
| 2,562,587 A | * | 7/1951 | Swearingen | A61C 3/06 125/39 |
| 2,748,483 A | * | 6/1956 | Hoffmeister | A61C 3/02 433/166 |
| 3,894,673 A | * | 7/1975 | Lowder | B23K 1/19 125/39 |
| 4,018,576 A | * | 4/1977 | Lowder | B23K 1/19 51/307 |
| 4,776,862 A | * | 10/1988 | Wiand | B24D 3/007 228/122.1 |

(Continued)

OTHER PUBLICATIONS

ASM International, Vacuum Induction Melting, 2008, ASM Handbook, vol. 15: Casting pp. 1-8.*

*Primary Examiner* — Jacob Cigna
(74) *Attorney, Agent, or Firm* — Warn Partners, P.C.

(57) ABSTRACT

Process for manufacture of a dental burr including a brazed diamond grit working surface comprising the steps of: a. providing a vacuum induction furnace and a graphite insert which is tuned to be heated at a predetermined frequency in the induction furnace, said graphite insert including a sub chamber configured for receiving at least one dental burr; b. providing a dental burr blank including a shaft portion and a working head portion; c. providing a synthetic diamond abrasive grit material, which is unprocessed for removal of ferromagnetic properties, mixture with a temporary green binder which adheres to the burr substrate and coating the working head portion with the mixture; d. placing the coated burr into the graphite insert sub chamber and heating the graphite insert to 910 to 990° C.; and e. heating the coated burr in the chamber under a vacuum for forming a diamond burr with a brazed diamond grit working surface.

11 Claims, 5 Drawing Sheets

(56) References Cited

U.S. PATENT DOCUMENTS

| | | | | |
|---|---|---|---|---|
| 4,834,655 A * | 5/1989 | Kyotani | ................... | B24D 7/10 |
| | | | | 433/166 |
| 4,968,326 A * | 11/1990 | Wiand | ..................... | B24D 3/06 |
| | | | | 51/293 |
| 5,492,771 A * | 2/1996 | Lowder | ................ | B23K 35/327 |
| | | | | 428/546 |
| 5,511,718 A * | 4/1996 | Lowder | .................. | B24D 18/00 |
| | | | | 228/103 |
| 6,649,887 B2 * | 11/2003 | Budinger | ............... | B23K 1/002 |
| | | | | 219/615 |
| 8,337,204 B2 * | 12/2012 | Lowder | ................... | A61C 3/06 |
| | | | | 433/166 |
| 2002/0139794 A1 * | 10/2002 | Budinger | ............... | B23K 1/002 |
| | | | | 219/615 |
| 2006/0068358 A1 * | 3/2006 | Lowder | ................... | A61C 3/06 |
| | | | | 433/66 |

* cited by examiner

INDUCTION HEATED VACUUM FURNACE FOR MAKING BRAZED DIAMOND DENTAL BURRS

FIELD OF THE INVENTION

The present invention relates to a process for precision manufacture of brazed diamond dental burrs.

BACKGROUND OF THE INVENTION

Diamond dental burrs are made using a nickel electroplating process that co-deposits diamond and nickel onto a small dental burr core or mandrel are made using natural diamond not synthetic diamond. The only known supplier of brazed diamond dental burrs also uses natural diamond as stated in their product specifications.

Brazing of diamond to metal substrates such as used in ophthalmic grinding wheels and other abrasive tools is known such as shown in my prior U.S. Pat. Nos. 4,776,862 and 4,968,326. As inventor of these patents, it occurred to me that brazed diamond dental burrs would provide a dentist with a longer life higher quality tool. Additionally, brazing would be more environmentally friendly than electroplated tool and would result in cost savings.

Typically, vacuum furnaces are used for brazing of diamonds onto abrasive tools. The substrates I have used in the past are typically large and robust and this method of heating has been used very effectively to provide diamond abrasive surfaces to brazed tools.

However, I have found that using conventional vacuum furnace brazing techniques with the delicacy involved in the size of diamond burr type tools resulted in warp-age and uneven and unacceptable results.

Therefore, there remains a need in the art for an improved process to provide efficient and effective manufacture of brazed diamond dental burrs.

SUMMARY OF THE INVENTION

In the present invention, there is provided process for manufacture of a dental burr including a brazed diamond grit working surface comprising the steps of:
a. Providing a vacuum induction furnace and a graphite insert which is tuned to be heated at a predetermined frequency in the induction furnace, said graphite insert including a sub chamber configured for receiving at least one dental burr;
b. Providing a diamond dental burr blank including a shaft portion and a working head portion;
c. Providing a diamond like hardness abrasive grit material distributed on a mixture of a temporary green binder and a brazing alloy which adheres to the burr substrate;
d. Placing the coated burr into the graphite insert sub chamber induction heated hot zone; and
e. Precision heating the coated burr in the chamber under a vacuum for forming a diamond burr with a brazed diamond grit working surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
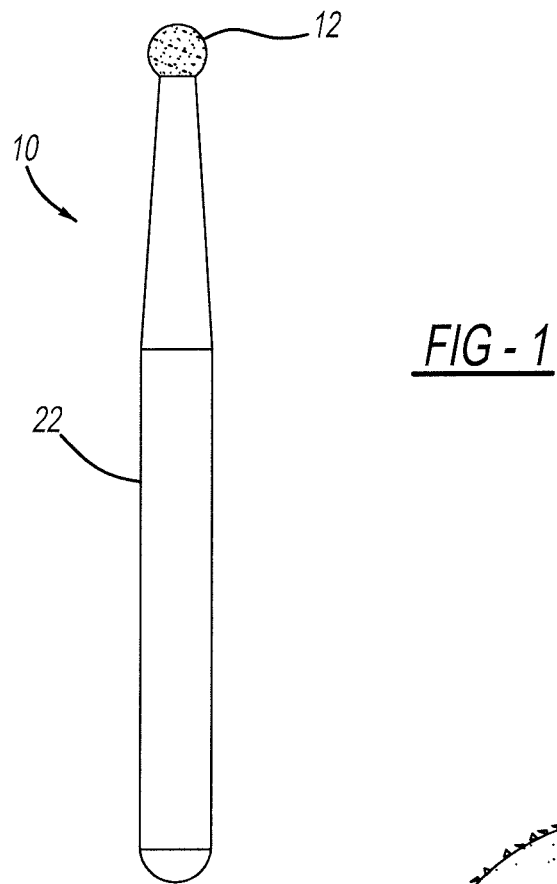
FIG. 1 is a side view of a typical dental burr in accordance with the present invention.
Figure 2:
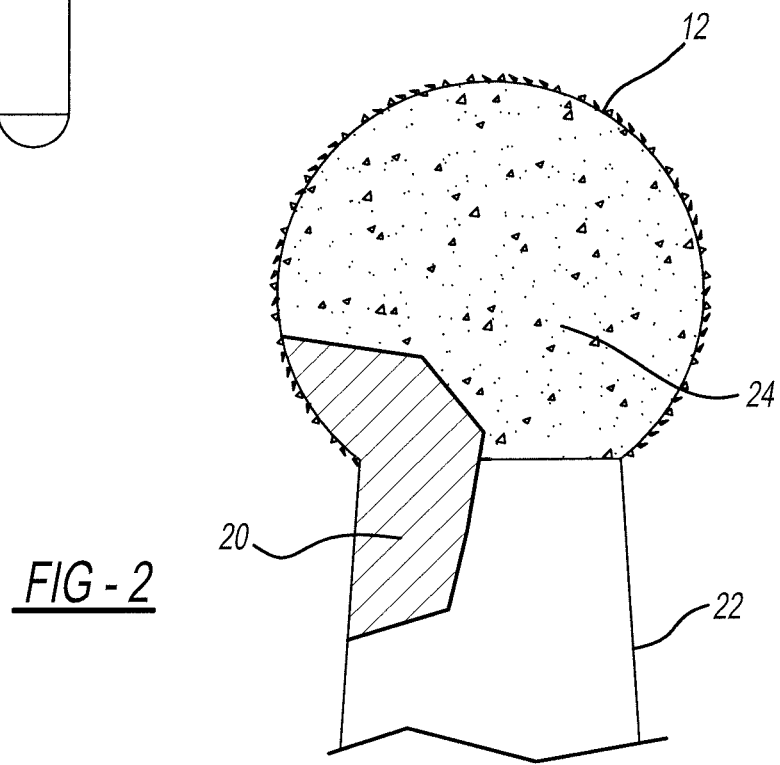
FIG. 2 is a detailed view of the dental burr of FIG. 2 partially broken away.
Figure 3:
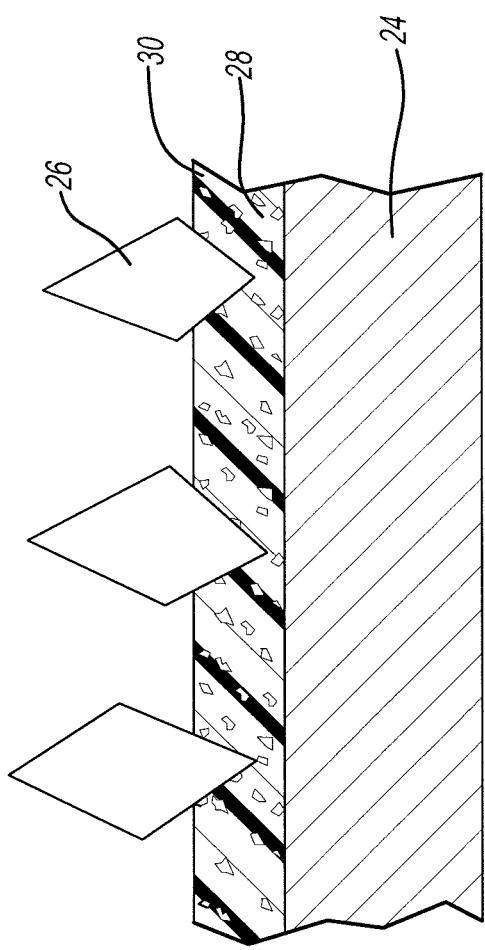
FIG. 3 is a sectional view of a "green" structure prior to brazing of the dental burrs of the present invention.
Figure 4:
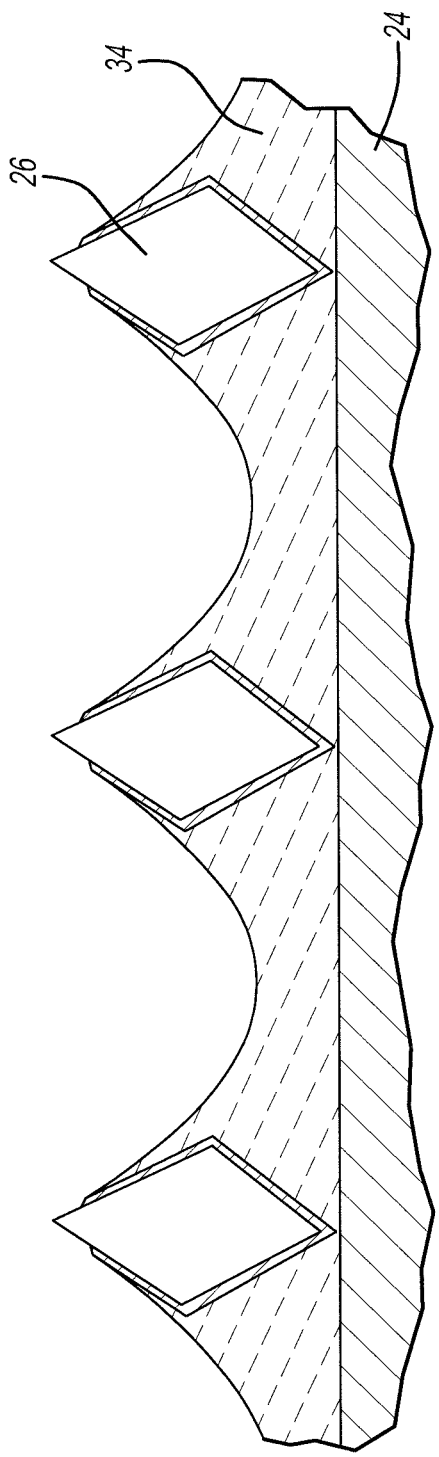
FIG. 4 is a detailed sectional view showing the brazed structure of the dental burrs of the present invention.
Figure 5:
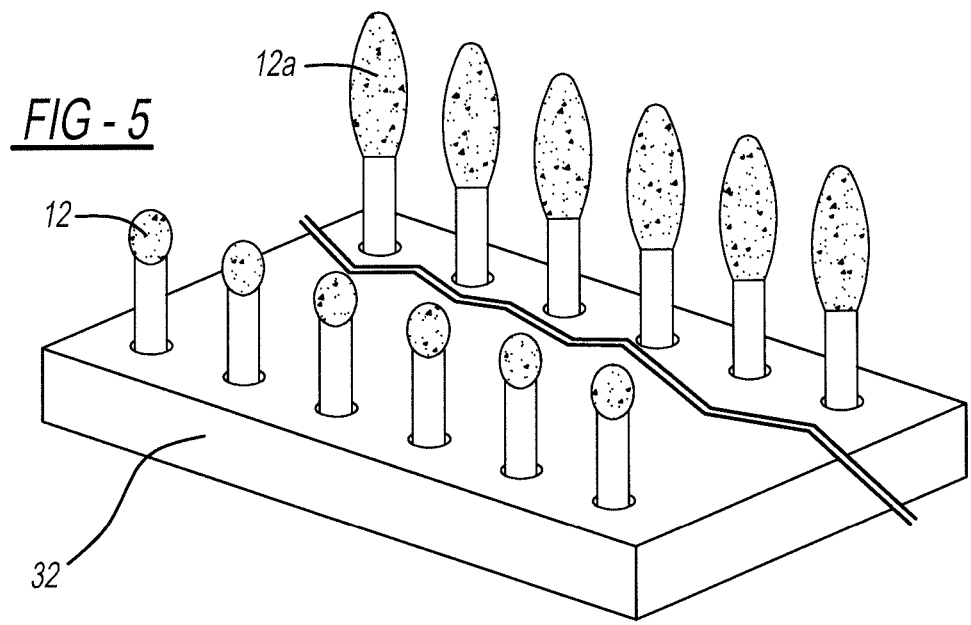
FIG. 5 is a perspective view showing dental burrs in a graphite tray.
Figure 6:
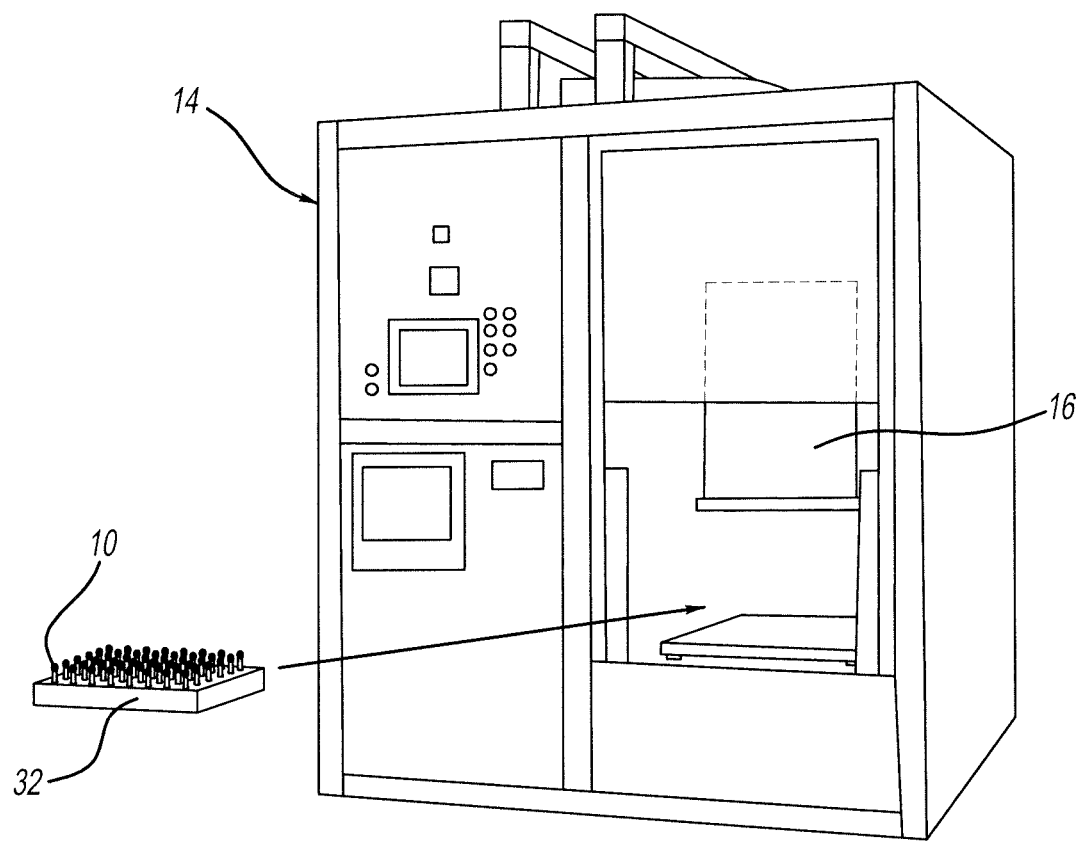
FIG. 6 is a view showing the tray of FIG. 5 being loaded into a vacuum graphite induction heated vacuum furnace in preparation for brazing.
Figure 7:
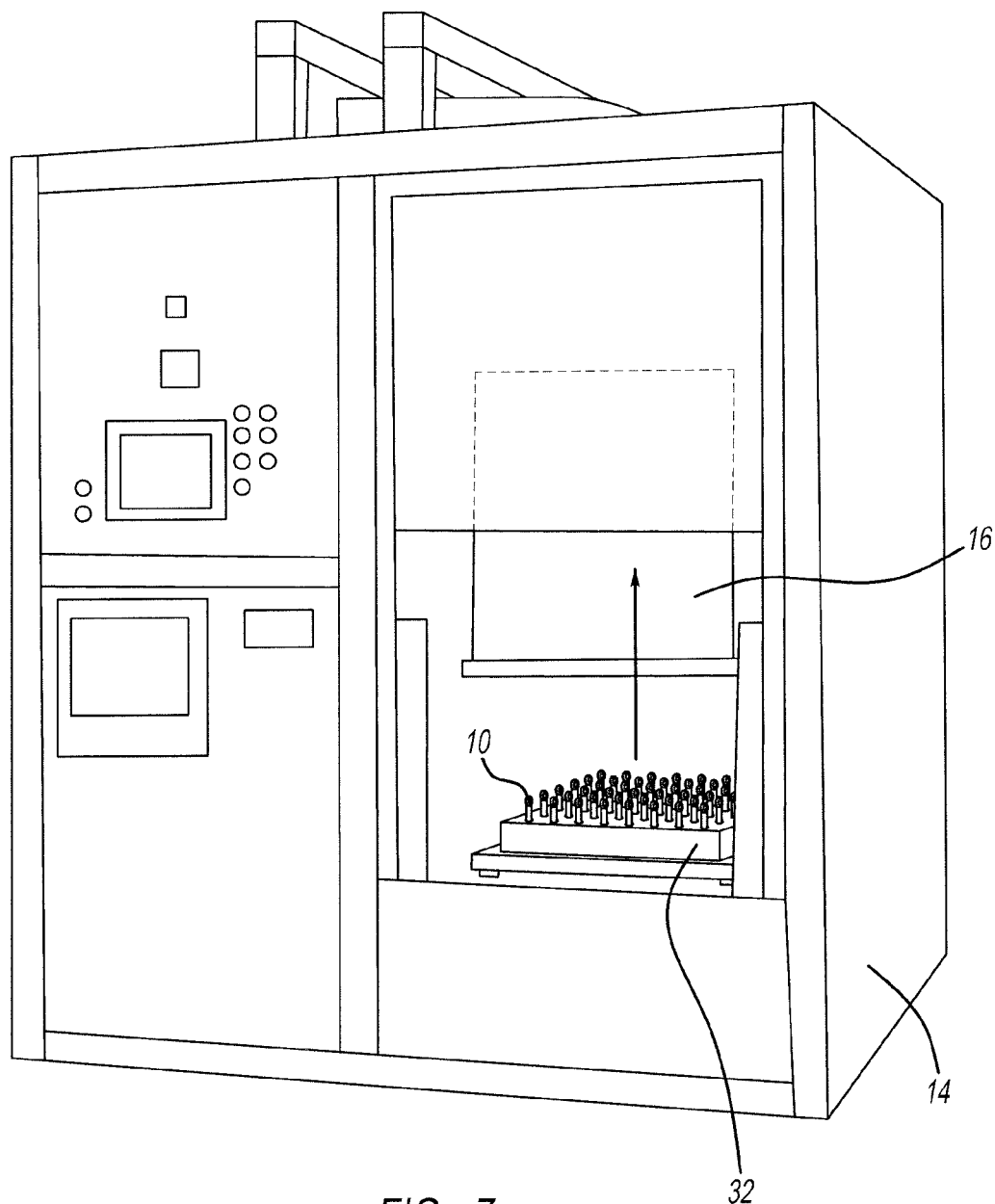
FIG. 7 is a perspective view of the tray of FIG. 5 being lifted in the oven for heating and brazing.
Figure 8:
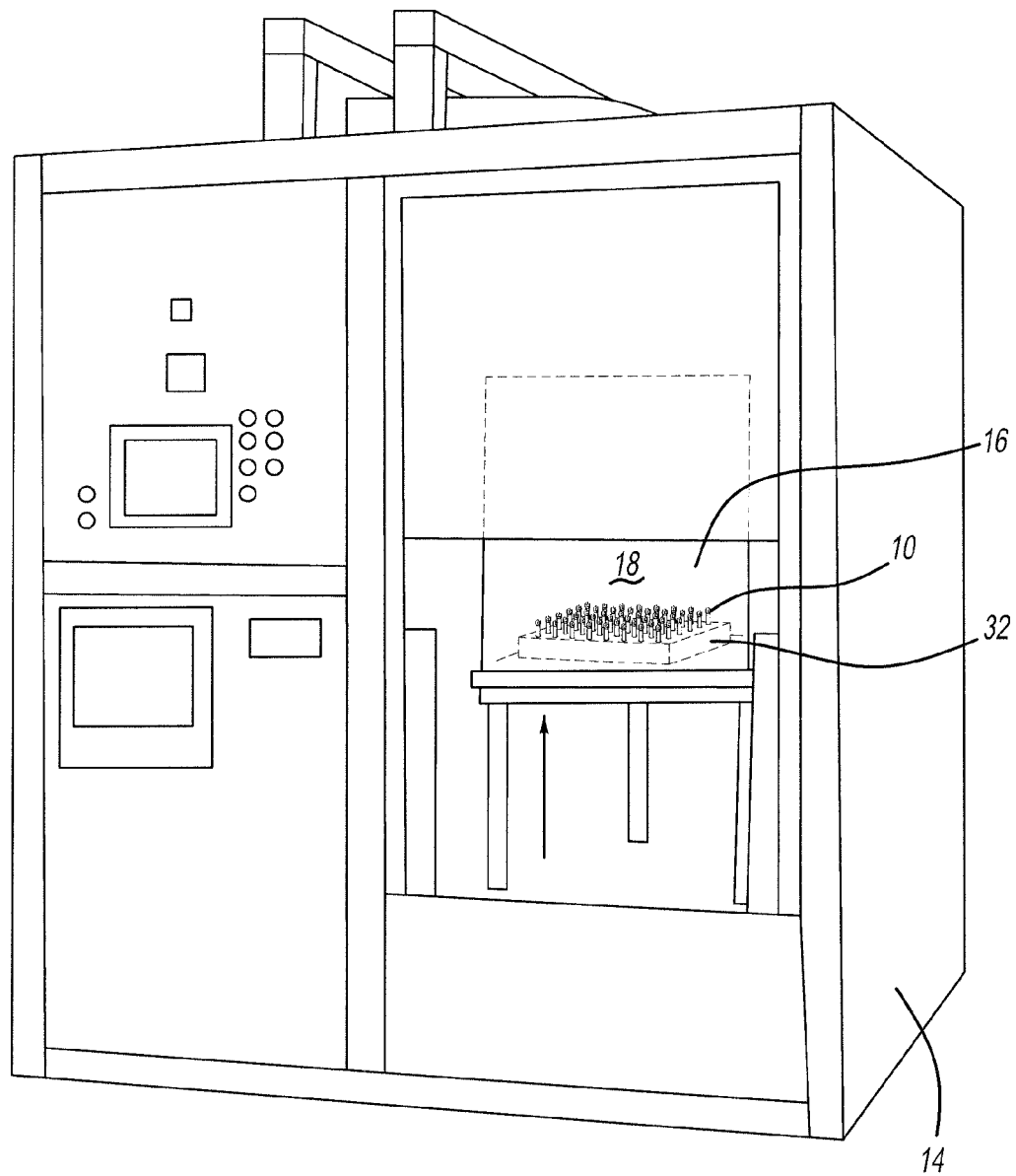
FIG. 8 is a perspective view off the tray in the oven with the dental burrs being heated under vacuum by induction heating and being brazed.

In the present invention, there is provided a process for manufacture of a dental burr 10 including a brazed diamond grit working surface 12 comprising the steps of:
a. Providing a vacuum induction furnace 14 and a graphite insert 16 which is tuned to be heated at a predetermined frequency in the induction furnace 14, the graphite insert 16 including a sub chamber 18 configured for receiving at least one dental burr 10;
b. Providing a diamond dental burr blank 20 including a shaft portion 22 and a working head portion 24;
c. Providing a diamond like hardness abrasive grit material 26 in a mixture 28 with a temporary green binder 30 which adheres to the burr substrate 24 and coating the working head portion with the mixture;
d. Placing the coated burr into a graphite insert 32 into a graphite sub chamber 18 of the furnace 14 (See FIGS. 7 and 8); and
e. Precision heating the coated burr 10 in the chamber 18 under a vacuum for forming a diamond burr 10 with a brazed 34 diamond grit working surface.

The graphite insert 16 forming chamber 18 is tuned to a specific frequency for heating by the vacuum induction furnace 14. In the present invention, a preferred graphite chamber has a size/heating zone of about 15 inch diameter and 15 inches long. With this size, a manufacturing quantity of dental burrs 10 can be heated at once. As an example a 1" thick graphite plate that is 10×10 inches with 1.6 mm diameter holes 0.50 inches deep in an array of 100 holes is used for placement of the dental burrs into the furnace.

An induction heated vacuum furnace is generally known in the furnace art. However, an induction heated vacuum furnace with a graphite heating zone used for manufacture of dental burrs is very unique. They are generally used to smelt or melt metals. However, the heat created is inducting into the metal or crucible being heated. With this new type of induction heated furnace, a radio frequency is tuned to induct into a graphite cylinder that forms the heating zone, the interior of the graphite is where the parts are placed and the graphite is heated instead of the work piece. In the present invention a GH Group Model VF-40 furnace is suitable for use.

In a vacuum furnace of this type, the total cycle time can be 1 hour or less compared to the conventional 8 hour cycle. The temperature control can be + or −1 degree C. in the heating zone of 15 inch diameter and 15 inches long, compared to a conventional radiant heated furnace of + or −5 degrees C. This is necessary to provide uniform manufacture of the burrs without inconsistencies in brazing or damage or warping of the burrs or the brazing material.

Diamond grit useful in the present invention is typically natural diamond but may be any diamond like hardness grit material which is carbide forming or can be made to be carbide forming by coating it with a powder of a carbide forming material such as Si, Mo, Cr, Fe, Ti, TiH. Thus, the grit used is selected from diamond, cubic boron nitride, silicon carbide and tungsten carbide. A particularly preferred grit material is a synthetic diamond grit as set forth in my copending application entitled Vacuum Brazed Diamond Dental Burr made using Synthetic Diamond filed contemporaneously herewith on Apr. 17, 2015 which is incorporated herein by reference thereto. The sizes of the grit material may vary depending on the application but are generally 60/80 to 325/400 typically 80/100 to 230/270 and preferably 100/120 to 200/230.

A diamond dental burr blank including a shaft portion 22 and a working head portion 24. These may be in any readily known and used dental configurations.

A diamond like hardness abrasive grit material mixture with a temporary green binder which adheres to the burr substrate is provided. The binder used is typically enough to maintain tackiness to the working head portion by merely dipping brushing or otherwise applying the material to the working head portion of the dental burr. The binder used must be volatile during heating so that it does not interfere with the brazing process.

The dental burr or a plurality of dental burrs 10 are inserted into the cavity in the graphite insert 32 and then placed in the oven 14 as shown in. The graphite insert is heated to temperatures and under conditions as follows. Generally, 875 C to 1100 C typically 890 C to 1000 C and preferably 910 C to 990 C are used for brazing of the dental burrs. The oven is kept at a vacuum of 4×10−3 torr to 5×10−8 torr or 5×10−4 torr to 4×10−8 torr or 4×10−5 torr to 4×10−7 torr.

In a vacuum furnace of this type, the total cycle time can be 1 hour or less compared to the conventional 8 hour cycle. The temperature control can be + or −1 degree C. in the heating zone of 15 inch diameter and 15 inches long, compared to a conventional radiant heated furnace of + or −5 degrees C.

It is believed with the present process the following advantages are realized;
1. Reduced cost by:
   Reduced energy cost
   Reduce overhead (burden) costs
   Reduced furnace maintenance cost
   Reduced coolant (water) cost
   Shorter cycle times
   Increased through-put
2. Improved quality:
   More uniformity from burr to burr
   Higher quality
   Longer life
   Greater cutting efficiency
   Less degradation to burr core
   Less total wicking of braze metals over total diamond partial Also, the cost of the brazed burr is much less than the cost of the equivalent electroplated burr.

Example 1

Brazed diamond burrs are made by using standard dental burr blanks and attaching 60/80; 80/100, 100/120, 230/270 and 325/400 to the head portion of the diamond burrs with a temporary binder and a carbide forming braze material intermixed as shown in my U.S. Pat. Nos. 4,968,326 and 4,776,862, all of which are incorporated herein by reference thereto.

Production type runs 100 of the burrs with various grit sizes were placed in a GH Group Model VF-40 furnace. And heated for 1 hour at about 5×10−4 torr to 4×10−8 torr. 5×10−4 torr to 4×10−8 torr and 10−4 torr to about 4×10−8 torr. These processes are repeated at temperatures of 875 C, 890 C, 910 C to 990 C 1000 C and 1100 degrees Centigrade The resulting burrs are found to be suitable for use as dental burrs in the dentistry industry.

The description of the invention is merely exemplary in nature and, thus, variations that do not depart from the essence of the invention are intended to be within the scope of the invention. Such variations are not to be regarded as a departure from the spirit and scope of the invention.

What is claimed is:

1. A process for manufacture of a dental burr including a brazed diamond grit working surface comprising the steps of:
   providing a vacuum induction furnace and a graphite insert which is tuned to be heated at a predetermined frequency in the induction furnace, said graphite insert including a sub chamber configured for receiving at least one dental burr;
   providing a dental burr blank including a shaft portion and a working head portion;
   providing a synthetic diamond abrasive grit material, which is unprocessed for removal of ferromagnetic properties, mixture with a temporary green binder which adheres to the burr substrate and coating the working head portion with the mixture;
   placing the coated burr into the graphite insert sub chamber and heating the graphite insert to 910 to 990° C.; and
   heating the coated burr in the chamber under a vacuum for forming a diamond burr with a brazed diamond grit working surface.

2. The process for manufacture of a dental burr including a brazed diamond grit working surface of claim 1, wherein said chamber of said graphite insert is configured for containing a heating of a plurality of said diamond dental burrs with a brazed diamond grit working surface.

3. The process for manufacture of a dental burr including a brazed diamond grit working surface of claim 1, wherein the synthetic diamond abrasive grit material is either capable of carbide formation on its surface or treated for carbide formation by coating with a carbide forming substance.

4. The process for manufacture of a dental burr including a brazed diamond grit working surface of claim 1, wherein the grit size is from about 60/80 to about 325/400.

5. The process for manufacture of a dental burr including a brazed diamond grit working surface of claim 1, wherein the grit size is from about 80/100 to 230/270.

6. The process for manufacture of a dental burr including a brazed diamond grit working surface of claim 1, wherein the grit size is from about 100/120 to about 230/270.

7. The process for manufacture of a dental burr including a brazed diamond grit working surface of claim 1, wherein the vacuum induction furnace is held at a vacuum in the range of from about $4 \times 10^{-3}$ torr to about $5 \times 10^{-8}$ torr.

8. The process for manufacture of a dental burr including a brazed diamond grit working surface of claim 1, wherein the vacuum induction furnace is held at a vacuum in the range of from about $5 \times 10^{-4}$ torr to $4 \times 10^{-8}$ torr.

9. The process for manufacture of a dental burr including a brazed diamond grit working surface of claim 1, wherein the vacuum induction furnace is held at a vacuum in the range of from about $4 \times 10^{-5}$ torr to $4 \times 10^{-7}$ torr.

10. The process of claim 1 wherein a plurality of burrs are placed in a graphite tray fixture for placement in the heating chamber of the vacuum induction furnace.

11. The process of claim 1 wherein the temperature of brazing is controlled to within plus or minus 1 degree Centigrade during the process.

* * * * *